(12) United States Patent
Sakaguchi et al.

(10) Patent No.: US 9,928,992 B2
(45) Date of Patent: Mar. 27, 2018

(54) PLASMA GENERATION DEVICE

(71) Applicant: Panasonic Intellectual Property Management Co., Ltd., Osaka (JP)

(72) Inventors: Yoshihiro Sakaguchi, Hyogo (JP); Shin-Ichi Imai, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 15/169,768

(22) Filed: Jun. 1, 2016

(65) Prior Publication Data
US 2016/0358752 A1 Dec. 8, 2016

(30) Foreign Application Priority Data

Jun. 5, 2015 (JP) .................. 2015-115185

(51) Int. Cl.
| H01J 37/32 | (2006.01) |
| A61L 2/14 | (2006.01) |
| H05H 1/48 | (2006.01) |
| H05H 1/46 | (2006.01) |
| C02F 1/46 | (2006.01) |

(52) U.S. Cl.
CPC .......... *H01J 37/32064* (2013.01); *A61L 2/14* (2013.01); *H01J 37/32036* (2013.01); *H01J 37/32045* (2013.01); *H01J 37/32816* (2013.01); *H01J 37/32825* (2013.01); *H05H 1/48* (2013.01); *C02F 1/4608* (2013.01); *C02F 2303/04* (2013.01); *H05H 2001/4682* (2013.01)

(58) Field of Classification Search
None
See application file for complete search history.

(56) References Cited

U.S. PATENT DOCUMENTS

| 3,304,717 | A | * | 2/1967 | Fournet | B64G 1/406 313/231.01 |
| 4,589,398 | A | * | 5/1986 | Pate | F02P 9/007 123/594 |
| 5,399,832 | A | * | 3/1995 | Tanisaki | B01J 8/24 219/121.43 |
| 6,239,559 | B1 | * | 5/2001 | Okamoto | H05B 41/24 315/111.21 |
| 6,313,587 | B1 | * | 11/2001 | MacLennan | H01J 61/025 315/224 |
| 7,460,225 | B2 | * | 12/2008 | Karanassios | G01N 21/67 356/246 |

(Continued)

FOREIGN PATENT DOCUMENTS

| JP | 2004-273312 | 9/2004 |
| JP | 2012-018890 | 1/2012 |

(Continued)

*Primary Examiner* — Douglas W Owens
*Assistant Examiner* — Srinivas Sathiraju
(74) *Attorney, Agent, or Firm* — McDermott Will & Emery LLP

(57) ABSTRACT

A plasma generation device includes: a pair of electrodes that cause plasma to be generated in atmospheric pressure by a voltage being applied between the pair of electrodes; and a power source that includes a step-up transformer that has a coupling coefficient of 0.9 or greater and 0.9999 or less and generates the voltage.

12 Claims, 5 Drawing Sheets

(56) References Cited

U.S. PATENT DOCUMENTS

| | | | | |
|---|---|---|---|---|
| 7,999,173 B1* | 8/2011 | Ashpis | H01L 31/042 | 136/244 |
| 8,323,753 B2* | 12/2012 | De Vries | C23C 16/402 | 427/569 |
| 8,324,591 B2* | 12/2012 | Choi | H05H 3/06 | 250/423 R |
| 8,333,166 B2* | 12/2012 | Bolden, II | H01J 37/32082 | 118/723 E |
| 8,444,870 B2* | 5/2013 | Godyak | H01J 37/321 | 118/723 I |
| 8,465,809 B2* | 6/2013 | Sanjurjo | B01J 8/08 | 427/213 |
| 8,692,466 B2* | 4/2014 | Benzerrouk | H01J 37/32009 | 315/111.21 |
| 9,006,976 B2* | 4/2015 | Watson | A61M 16/12 | 315/111.21 |
| 9,236,227 B2* | 1/2016 | Watson | A61M 16/12 | |
| 9,390,894 B2* | 7/2016 | Eden | A23L 3/34095 | |
| 9,558,918 B2* | 1/2017 | Watson | A61M 16/12 | |
| 9,585,390 B2* | 3/2017 | Fridman | A01N 37/46 | |
| 2002/0167282 A1* | 11/2002 | Kirkpatrick | H01J 61/025 | 315/248 |
| 2004/0161361 A1* | 8/2004 | Uhm | A61L 2/14 | 422/30 |
| 2005/0275997 A1* | 12/2005 | Burke | B03C 3/41 | 361/220 |
| 2006/0011465 A1* | 1/2006 | Burke | H05H 1/2406 | 204/164 |
| 2006/0124445 A1* | 6/2006 | Labrecque | B01D 53/323 | 204/170 |
| 2006/0278254 A1* | 12/2006 | Jackson | B08B 7/0021 | 134/21 |
| 2007/0161308 A1* | 7/2007 | Bourham | D06M 10/025 | 442/123 |
| 2008/0050537 A1* | 2/2008 | Godyak | H01J 37/321 | 427/575 |
| 2009/0038933 A1* | 2/2009 | Boutot | B01J 19/088 | 204/171 |
| 2009/0291235 A1* | 11/2009 | Sanjurjo | B01J 8/08 | 427/580 |
| 2009/0297409 A1* | 12/2009 | Buchanan | H05H 1/2406 | 422/186.29 |
| 2010/0136262 A1* | 6/2010 | Godyak | H01J 37/321 | 427/571 |
| 2011/0180149 A1* | 7/2011 | Fine | B01J 21/063 | 137/1 |
| 2012/0261391 A1* | 10/2012 | Ihde | B22F 1/02 | 219/121.52 |
| 2014/0014516 A1* | 1/2014 | Kumagai | C02F 1/4608 | 204/556 |

FOREIGN PATENT DOCUMENTS

| | | |
|---|---|---|
| JP | 2014-210222 | 11/2014 |
| WO | 2007/106374 | 9/2007 |

* cited by examiner

| COUPLING COEFFICIENT | POWER CONSUMPTION [W] |
|---|---|
| 0.894 | 75 |
| 0.916 | 64 |
| 0.956 | 65 |
| 0.988 | 65 |
| 0.991 | 79 |
| 0.997 | 110 |

PLASMA GENERATION DEVICE

BACKGROUND

1. Technical Field

The present disclosure relates to a plasma generation device.

2. Description of the Related Art

Japanese Unexamined Patent Application Publication No. 2012-18890 discloses a power source device that continuously applies large-current high-voltage pulses at a high speed in order to continuously generate plasma within a liquid.

SUMMARY

One non-limiting and exemplary embodiment provides a plasma generation device capable of realizing at least one selected from the group consisting of a power source size reduction, cost reduction, and power consumption reduction.

In one general aspect, the techniques disclosed here feature a plasma generation device including: a pair of electrodes that cause plasma to be generated in atmospheric pressure by a voltage being applied between the pair of electrodes; and a power source. The power source includes a step-up transformer that has a coupling coefficient of 0.9 or greater and 0.9999 or less and generates the voltage that is applied between the pair of electrodes.

According to the plasma generation device of the present disclosure, it is possible to realize at least one selected from the group consisting of a power source size reduction, cost reduction, and suppression of power consumption.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
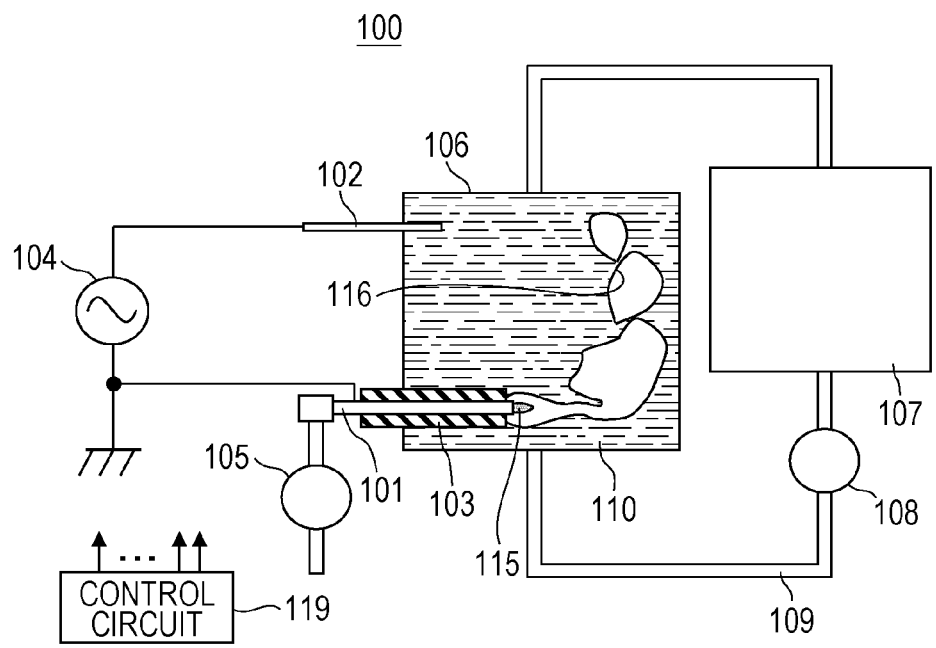
FIG. 1 is a block diagram depicting an example configuration of a plasma generation device in embodiment 1.

Findings Forming Basis of the Present Disclosure

Conventionally, in order to generate plasma by pulse discharge, it has been necessary to apply large-current high-voltage pulses in a space in which discharge is generated. Furthermore, when a discharge starting voltage increases due to the state of the discharge space (liquid type or gas type), maintaining the discharge starting voltage and continuing discharge has resulted in an increase in power consumption and an increase in device size. Furthermore, it has been necessary for conventional power source devices for plasma generation to generate plasma by using a transformer in order to raise the discharge starting voltage that causes discharge to occur, and there has been an increase in device size.

Thus, the inventors conducted diligent research in order to provide a plasma generation device capable of realizing at least one selected from the group consisting of a power source size reduction, cost reduction, and power consumption reduction by reducing the step-up ratio of a step-up transformer. Hereinafter, the findings forming the basis for the present disclosure will be described in greater detail.

The inventors discovered that the following problems occur in relation to the plasma generation device described in the "Description of the Related Art" section.

In a conventional plasma generation device, in order to generate a power source voltage with which plasma discharge is able to occur, a large step-up transformer is required in order for the step-up ratio to increase, and the power generation system becomes larger. Furthermore, there are problems relating to heat generation and power increases when a high voltage is to be maintained, and it has been necessary to increase size in order to extend the discharge time.

The inventors discovered that, by providing a power source of a plasma generation device with a step-up transformer that has a coupling coefficient of a value of 0.9 or greater and 0.9999 or less, it is possible to generate a larger voltage than the voltage determined by the step-up ratio.

In other words, by providing the power source with a step-up transformer having a coupling coefficient of a value of 0.9 or greater and 0.9999 or less (in other words, 90% or greater and 99.99% or less), it is possible to realize a state that is equivalent to there being an inductor having an inductance value (L value) of 0.01% or greater and 10% or less with respect to the L value of a secondary side of the step-up transformer, between the secondary side of the step-up transformer and a pair of electrodes that cause discharge to occur. This inductor may be a physical element, or may be brought about by the leakage inductance of a secondary winding. Then, if the region between the pair of electrodes that cause discharge to occur is deemed to be a capacitive load, and a resistance component of the secondary winding, the inductor, and the capacitive load between the pair of electrodes are viewed as an RLC series circuit, due to the resonance action thereof, a larger voltage than the voltage determined by the step-up ratio of the step-up transformer is generated at both ends of the capacitive load. Generally, with regard to a capacitance C, when an RLC series circuit resonates, a large voltage that is Q times that of the power source voltage (here, the voltage generated in the secondary winding of the step-up transformer) is generated. Q is also referred to as a Q value and a Q factor (quality factor), is a parameter indicating the sharpness of resonance, and is represented by $(1/R)\sqrt{(L/C)}$, in which it is assumed that R is the resistance component of the secondary winding, L is the inductance of the inductor or the leakage inductance of the secondary winding, and C is the electrostatic capacity between the electrodes.

In this way, a larger voltage than the voltage determined by the step-up ratio of the step-up transformer is generated between the pair of electrodes by the action of an LC resonance, and it is possible for discharge to be generated between the pair of electrodes.

Thus, a plasma generation device according to an aspect of the present disclosure includes: a pair of electrodes that cause plasma to be generated in atmospheric pressure by a voltage being applied between the pair of electrodes; and a power source. The power source includes a step-up transformer that has a coupling coefficient of 0.9 or greater and 0.9999 or less and generates the voltage that is applied between the pair of electrodes.

Accordingly, a larger voltage than the voltage determined by the step-up ratio of the step-up transformer is generated between the pair of electrodes by the LC resonance of the inductor of the output side (namely the secondary winding side) of the step-up transformer and by the capacitive load between the pair of electrodes. Discharge can be generated between the pair of electrodes using this large voltage. Consequently, it is not necessary to increase the step-up ratio itself in order to generate discharge, and it is possible to realize a size reduction and a suppression of power consumption. The coupling coefficient of the step-up transformer may be 0.9 or greater and 0.99 or less.

A plasma generation device according to an aspect of the present disclosure includes: a pair of electrodes that cause plasma to be generated in atmospheric pressure by a voltage being applied between the pair of electrodes; and a power source. The power source includes: a step-up transformer that generates the voltage that is applied between the pair of electrodes; and an inductor that is provided between a secondary side of the step-up transformer and the pair of electrodes, and has an inductance value of 0.01% or greater and 10% or less with respect to the inductance value of the secondary side of the step-up transformer.

Accordingly, a larger voltage than the voltage determined by the step-up ratio of the step-up transformer is generated between the pair of electrodes by the LC resonance of the inductor and the capacitive load between the pair of electrodes. Discharge can be generated between the pair of electrodes using this voltage. Consequently, it is not necessary to increase the step-up ratio itself in order to generate discharge, and it is possible to realize a size reduction and a suppression of power consumption.

The voltage may have a periodic voltage waveform having, in each period, a first voltage that generates discharge between the pair of electrodes, and a second voltage that causes the generated discharge to be maintained. The first voltage has an absolute value that is higher than an absolute value of the second voltage.

Accordingly, as a result of having the first voltage that generates discharge and the second voltage having an absolute value that is lower than the absolute value of the first voltage and causes the generated discharge to be maintained, it is not necessary to maintain the high-voltage first voltage and it is possible to realize a suppression of power consumption.

The power source may further include a rectification circuit that rectifies the voltage applied between the pair of electrodes.

Accordingly, by providing the rectification circuit, it becomes possible to switch between causing discharge with a forward voltage or a reverse voltage by altering the installation path (for example, changing a connection between the step-up transformer and the pair of electrodes), and it is possible to realize a suppression of power consumption. Furthermore, it is possible to control types of active species. It is because the types of active species produced by plasma are different between the case where plasma is generated with both a forward voltage and a reverse voltage, and the case where plasma is generated with only one of a forward voltage or a reverse voltage.

The pair of electrodes may be provided in a liquid, and may discharge and cause plasma to be generated in a gas-phase space in the liquid.

Accordingly, the pair of electrodes become a resistive load when the region between the pair of electrodes is provided in a liquid, and the pair of electrodes become a capacitive load when the positive pole is in a gas-phase space in the liquid. When the positive pole is in the gas-phase space in the liquid, a larger voltage than the voltage determined by the step-up ratio of the step-up transformer is generated by the LC resonance of the inductor and the capacitive load between the pair of electrodes. Discharge can be generated between the pair of electrodes using this voltage. Consequently, it is not necessary to increase the step-up ratio itself in order to generate discharge, and it is possible to realize a size reduction and a suppression of power consumption. It should be noted that, in the present specification, atmospheric pressure is an air pressure that is 913 hPa or greater and 1113 hPa or less, and includes the air pressure of the gas-phase space in the liquid. The pair of electrodes may generate the plasma in an atmospheric pressure of 963 hPa or greater and 1063 hPa or less.

Hereinafter, embodiments of the present disclosure will be described in detail using the drawings. It should be noted that the embodiments described hereinafter all represent a specific example of the present disclosure. The numerical values, the shapes, the materials, the constituent elements, the arrangement positions and modes of connection of the constituent elements, and the like given in the following embodiments are examples and are not intended to restrict the present disclosure. Furthermore, constituent elements that are not described in the independent claims indicating the most significant concepts of the present disclosure from among the constituent elements in the embodiments hereinafter are described as optional constituent elements forming part of a more desirable mode. Furthermore, the drawings are schematic views and do not always represent exact dimensions.

Embodiment 1

1.1 Configuration of Plasma Generation Device

First, the configuration of a plasma generation device 100 will be described.

FIG. 1 is a block diagram depicting an example configuration of a plasma generation device in embodiment 1.

As depicted in FIG. 1, the plasma generation device 100 includes a first metal electrode 101, a second metal electrode 102, an insulator 103, a power source 104, a supply pump 105, a reaction tank 106, a treatment tank 107, a circulation pump 108, a pipe 109, and a control circuit 119.

The first metal electrode 101 is a rod-shaped electrode, for example, provided such that at least a portion is exposed within the reaction tank 106 into which a liquid 110 that is to be treated is introduced. The liquid 110 is pure water or a treatment-target liquid, for example. In the case where the liquid 110 is pure water, the plasma generation device 100 generates a plasma liquid. In the case where the liquid 110 is a treatment-target liquid, the plasma generation device 100 exerts a sterilizing action on the liquid.

The second metal electrode 102 is a rod-shaped electrode, for example, provided such that at least a portion is exposed within the reaction tank 106.

The insulator 103 is formed so as to provide a ventilation gap around the outer periphery of the first metal electrode 101, and is mounted in an opening in the reaction tank 106.

The power source 104 has a step-up transformer that applies a voltage between the pair of electrodes made up of the first metal electrode 101 and the second metal electrode 102. As a result of the voltage being applied between the pair of electrodes from the step-up transformer, plasma 115 is generated between the pair of electrodes. Various active species such as OH radicals are produced in the liquid 110 due to the generation of the plasma 115.

The supply pump 105 supplies a gas to a gap between the first metal electrode 101 and the insulator 103. Gas bubbles 116 are thereby continuously generated at a tip-end portion of the insulator 103 and the first metal electrode 101. The plasma 115 is generated between the pair of electrodes even if these gas bubbles 116 are not present; however, due to the presence of the gas bubbles 116, it is possible to increase the efficiency of the generation of active species by the plasma 115. Furthermore, the pair of electrodes made up of the first metal electrode 101 and the second metal electrode 102 become a resistive load when the region between the pair of electrodes is provided in a liquid, and the pair of electrodes become a capacitive load when at least one of the first metal electrode 101 and that second metal electrode 102 is in a gas-phase space in the liquid.

At first, the reaction tank 106 stores pure water serving as untreated liquid for a plasma liquid, as the liquid 110, and stores the plasma liquid after the plasma 115 has been generated.

The treatment tank 107 is connected with the reaction tank 106 by a pipe, and water (the subsequent plasma liquid) is circulated between the treatment tank 107 and the reaction tank 106 by the circulation pump 108 when the plasma 115 is generated.

The control circuit 119 executes a program recorded in a memory, for example, and thereby controls the entire plasma generation device 100. The control circuit 119 may be an integrated circuit such as a central processing unit (CPU), a microcomputer, or the like.

1.2 Configuration of Power Source

Next, an example configuration of the power source 104 will be described.

Figure 2:
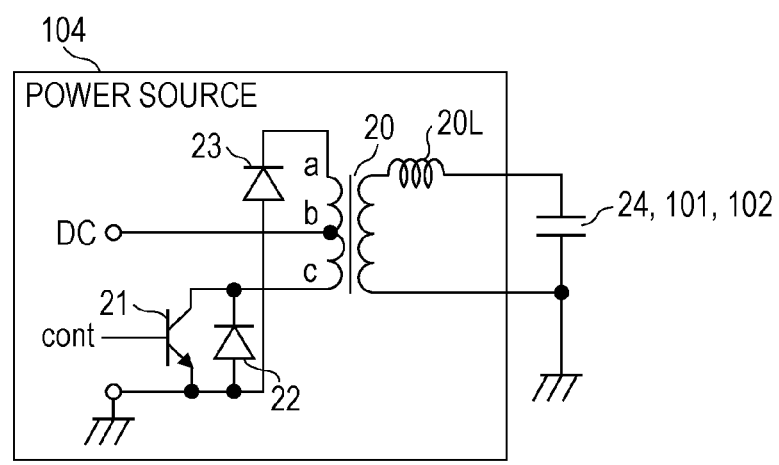
FIG. 2 is a circuit diagram depicting an example configuration of a power source and a capacitive load in embodiment 1.

FIG. 2 is a circuit diagram depicting an example configuration of the power source 104 and a capacitive load 24 in embodiment 1. As depicted in FIG. 2, the power source 104 includes a step-up transformer 20, an inductor 20L, a switch 21, a diode 22, and a diode 23. Furthermore, the capacitive load 24 of FIG. 2 depicts the pair of electrodes made up of the first metal electrode 101 and the second metal electrode 102 of FIG. 1.

The step-up transformer 20 has a primary winding, a secondary winding, and a core (an iron core, for example). The primary winding and the secondary winding are electromagnetically coupled via the core. The coupling coefficient of the step-up transformer 20 has a value of 0.9 or greater and 0.9999 or less. The primary winding has the three terminals of one end a, a middle tap b, and another end c. The winding ratio of the step-up transformer 20 is 1:1:40, for example. This winding ratio is the ratio of the three items of the number of turns from the one end a of the primary winding to the middle tap b, the number of turns from the middle tap b of the primary winding to the other end c, and the number of turns of the secondary winding. The secondary winding of the step-up transformer 20 applies a voltage between the pair of electrodes via the inductor 20L.

Figures 10, 11:
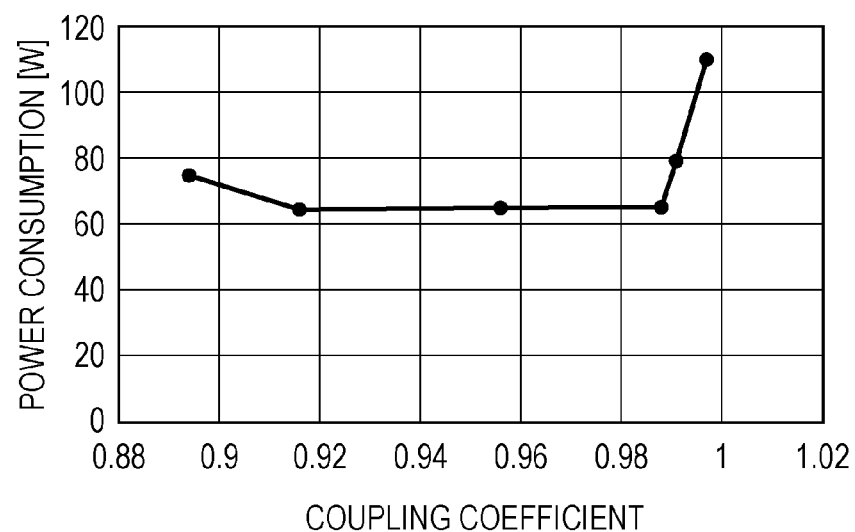
FIG. 10 is a graph depicting the relationship between a coupling coefficient of a step-up transformer and power consumption of the plasma generation device in embodiment 1.
FIG. 11 is a chart depicting the relationship between the coupling coefficient of the step-up transformer and the power consumption of the plasma generation device in embodiment 1.

FIGS. 10 and 11 are a graph and a chart depicting the relationship between the coupling coefficient of the step-up transformer 20 and the power consumption of the power source 104 in embodiment 1. As depicted in FIGS. 10 and 11, in the case where the coupling coefficient of the step-up transformer 20 is 0.9 or greater and 0.99 or less, power consumption can be particularly reduced. In the case the coupling coefficient is likewise 0.9 or greater and 0.99 or less also in embodiments 2 and 3 described hereinafter, power consumption can be particularly reduced.

The inductor 20L has an inductance value of 0.01% or greater and 10% or less with respect to the inductance value of the secondary winding. The inductor 20L may be the leakage inductance of the secondary winding of the step-up transformer 20, or maybe an inductor element separate from the secondary winding. An RLC series resonance circuit is formed from a resistance component R of the secondary winding, the inductance L of the inductor 20L, and the electrostatic capacity C of the capacitive load 24. Alternatively, an LC series resonance circuit is formed from the inductance L of the inductor 20L and the electrostatic capacity C of the capacitive load 24. As already described, a voltage that is double the magnitude of the power source voltage (here, the voltage generated in the secondary winding or the voltage generated in the resistance component R) is generated as a first voltage. The first voltage is applied to the capacitive load 24 when the RLC series circuit resonates, and the first is represented by $Vc=-V\cos\omega t+V$. Furthermore, the frequency thereof is represented by $f=1/2\pi\sqrt{LC}$. Therefore, a larger voltage than the voltage determined by the step-up ratio of the step-up transformer 20 is generated in the capacitive load 24. Consequently, it is not necessary for the step-up transformer 20 to be a step-up transformer in which the step-up ratio itself is large, and it is therefore possible to realize a reduction in size of the power source 104 and a suppression of power consumption.

The switch 21 is a switch transistor, and switches between whether or not to apply a direct-current voltage DC between the middle tap b and the other end c of the primary winding. The on and off states of the switch 21 is controlled by a switch control signal cont from the control circuit 119.

The diode 22 prevents a current flowing from the middle tap b to the other end c while the switch 21 is off.

The diode 23 prevents a current flowing from the one end a to the other end c and prevents a current flowing from the middle tap b to the one end a while the switch 21 is off.

The capacitive load 24 represents the pair of electrodes made up of the first metal electrode 101 and the second metal electrode 102. It should be noted that the direct-current voltage DC is input to the primary winding (more accurately, between the middle tap b and the other end c) of the step-up transformer 20 as an alternating current by performing switching; however, a sinusoidal wave of a commercial power supply or the like may be input.

1.3 Example of Voltage Waveform

Next, the voltage applied to the capacitive load 24 will be described.

Figure 3:
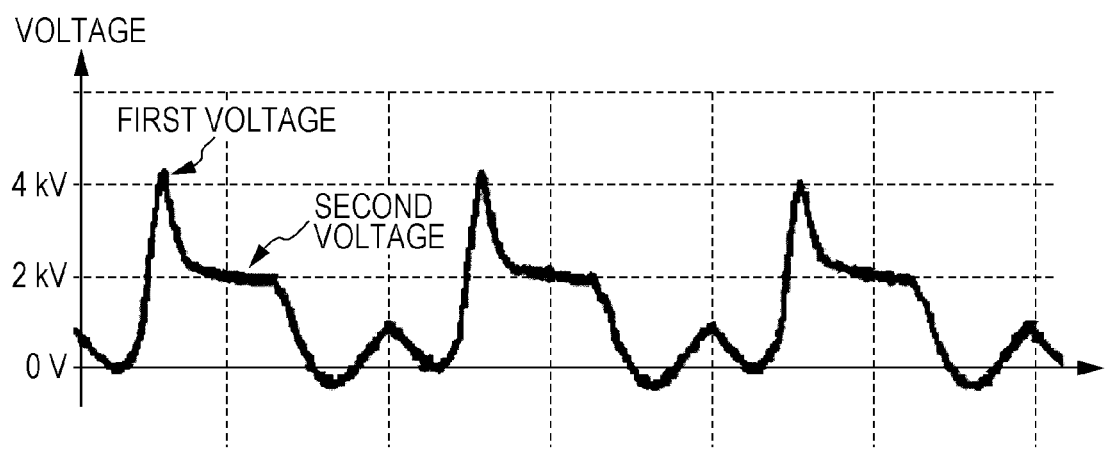
FIG. 3 is a drawing depicting an example waveform of a voltage generated between a pair of electrodes in embodiment 1.

FIG. 3 is a drawing depicting an example waveform of a voltage generated between the pair of electrodes (namely the capacitive load 24) in embodiment 1. In FIG. 3, the winding ratio of the step-up transformer 20 is the aforementioned 1:1:40, and the direct-current voltage DC that is input is 50 V.

As depicted in FIG. 3, the voltage waveform generated between the pair of electrodes has a periodic voltage waveform having, in each period, a first voltage and a second voltage. The first voltage has a voltage value with which discharge is generated between the pair of electrodes. The second voltage has a voltage value that is lower than the voltage value of the first voltage and causes the generated discharge to be maintained. The first voltage is superimposed on the second voltage, and there is a substantially monotonous decrease from the first voltage to the second voltage.

In FIG. 3, the first voltage is approximately 4 kV and the second voltage is approximately 2 kV. The second voltage is a voltage determined by the winding ratio of the step-up transformer 20, and is 40 times greater than 50 V. The first voltage is a voltage generated by the LC resonance of the inductor 20L and the capacitive load 24 between the pair of electrodes, and is a larger voltage than the voltage determined by the step-up ratio of the step-up transformer 20. The maximum value of the first voltage is double the second voltage or greater.

In this way, as a result of the voltage waveform that is applied between the pair of electrodes having the first voltage that generates discharge and the second voltage having a voltage value that is lower than the voltage value of the first voltage and causes the generated discharge to be maintained, it is not necessary to maintain the high-voltage first voltage and it is possible to realize a suppression of power consumption.

1.4 Example of Voltage Waveform and Switch Control Signal

Next, a switch control signal and an input voltage of the primary winding side will be described.

Figure 4:
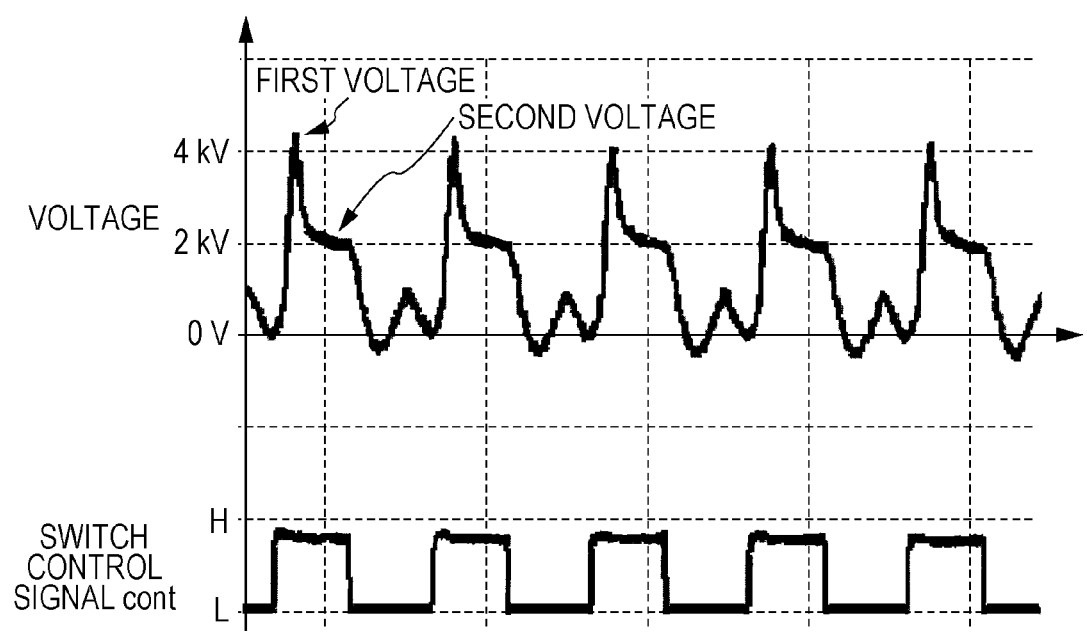
FIG. 4 is a drawing depicting an example waveform of a voltage generated between the pair of electrodes and a switch control signal in embodiment 1.

FIG. 4 is a drawing depicting an example waveform of a voltage generated between the pair of electrodes and a switch control signal cont of the primary winding side in embodiment 1.

The upper section of FIG. 4 is the same as FIG. 3. The lower section of FIG. 4 indicates the switch control signal cont that controls the on and off state of the switch 21. The switch 21 is in an on state when the switch control signal cont is H-level (high-level), and the switch 21 is in an off state when the switch control signal cont is L-level (low-level). As a result of the switch 21 turning on and off in accordance with the switch control signal cont, an alternating-current signal configured from a square wave having an amplitude of 50 V is input with a waveform that is substantially the same as that in the lower section of FIG. 4, between the middle tap b and the other end c of the primary winding of the step-up transformer 20.

The switch control signal cont is generated by the control circuit 119, and is supplied to the switch 21 from the control circuit 119. The frequency of the switch control signal cont is within the range of approximately 20 kHz to 100 kHz, for example. The second voltage applied as per the step-up ratio and the first voltage generated by the LC resonance are thereby superimposed and applied between the secondary-side pair of electrodes. As long as this is satisfied, the primary winding-side circuit of FIG. 2 may have another circuit configuration.

1.5 Example of Leakage Inductance and Maximum Voltage Applied Between Pair of Electrodes Next, an experiment result (simulation result) indicating the size of the inductor 20L and the first voltage will be described.

Figure 5:
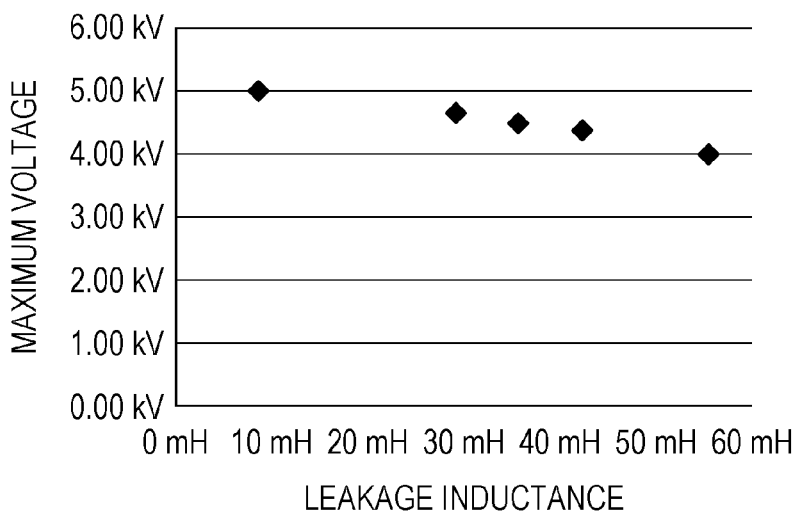
FIG. 5 is a drawing depicting leakage inductance and a maximum voltage applied between the pair of electrodes in embodiment 1.

FIG. 5 is a drawing depicting the relationship between leakage inductance and a maximum voltage applied between the pair of electrodes in embodiment 1. In FIG. 5, the inductor 20L is assumed to be leakage inductance. The step-up transformer 20 is assumed to have a winding ratio of 1:1:40 as in the above-mentioned example, and the frequency of the switch control signal cont is assumed to be 25 kHz. The maximum value of FIG. 5 is the maximum value of the first voltage.

In FIG. 5, the maximum value is 5.02 kV at a leakage inductance of 8.5 mH. Similarly, the maximum value is 4.63 kV at 28.9 mH, the maximum value is 4.49 kV at 35.4 mH, the maximum value is 4.36 kV at 42.1 mH, and the maximum value is 3.99 kV at 55.3 mH. At any of the measurement points, the maximum value of the first voltage is approximately double the voltage determined by the step-up ratio (the second voltage) or greater. In FIG. 5, it is thought that errors between the frequency of the voltage applied between the pair of electrodes and the resonance frequency decrease as the leakage inductance decreases.

As described hereinabove, according to the plasma generation device 100 in the present embodiment, the first voltage that is larger than the second voltage determined by the step-up ratio of the step-up transformer is generated between the pair of electrodes by the LC resonance of the inductor 20L of the output side (namely the secondary winding side) of the step-up transformer 20 and the capacitive load between the pair of electrodes. The first voltage has a voltage value with which discharge can be newly generated between the pair of electrodes, and the second voltage has a voltage value that causes the discharge to be maintained.

Consequently, it is not necessary to increase the step-up ratio itself in order to generate discharge, and it is possible to realize a size reduction and a suppression of power consumption.

Embodiment 2

In embodiment 1, an example configuration was described in which, in the power source 104, pulses are applied to only one side of the middle tap b (namely between the middle tap b and the other end c) of the primary winding of the step-up transformer 20. In contrast, in the present embodiment, an example configuration is described in which pulses are applied to both sides of the middle tap b (namely between the middle tap b and the other end c, and between the middle tap b and the one end a) of the primary winding of the step-up transformer 20.

Figure 6:
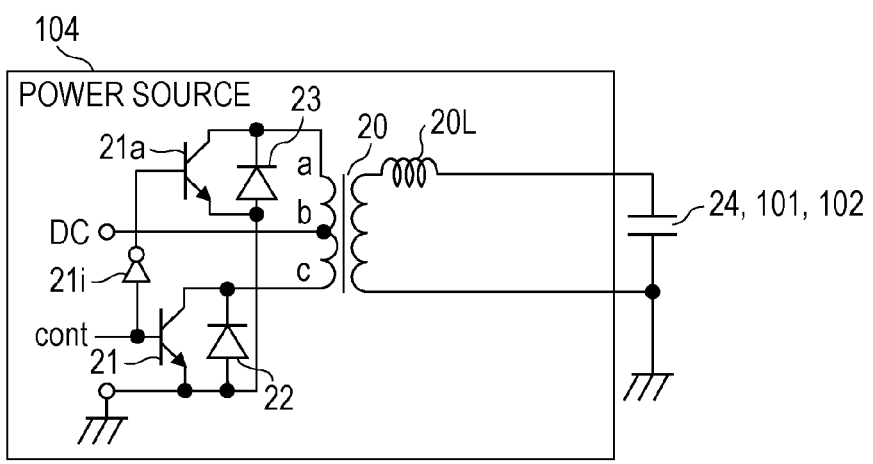
FIG. 6 is a circuit diagram depicting an example configuration of a power source and a capacitive load in embodiment 2.

FIG. 6 is a circuit diagram depicting an example configuration of the power source 104 and the capacitive load 24 in embodiment 2.

The power source 104 of FIG. 6 is different compared to FIG. 2 in that a switch 21*a* and an inverter 21*i* have been added. The remaining configuration of the power source 104 according to the present embodiment is the same as the configuration of the power source 104 according to embodiment 1. Hereinafter, the description will focus on the differences.

The switch 21*a* is a switch transistor, and switches between whether or not to apply a direct-current voltage DC between the middle tap b and the one end a of the primary winding. The on and off states of the switch 21*a* are controlled by a signal for which the switch control signal cont is inverted.

The inverter 21*i* inverts the switch control signal cont, and supplies the inverted switch control signal cont to the switch 21*a*. The switch 21*a* and the switch 21 are thereby exclusively on.

According to this configuration, the power source 104 of FIG. 6 exclusively applies pulses in an alternating manner to both sides of the middle tap b (namely between the middle tap b and the other end c, and between the middle tap b and the one end a) of the primary winding of the step-up transformer 20.

Figure 7:
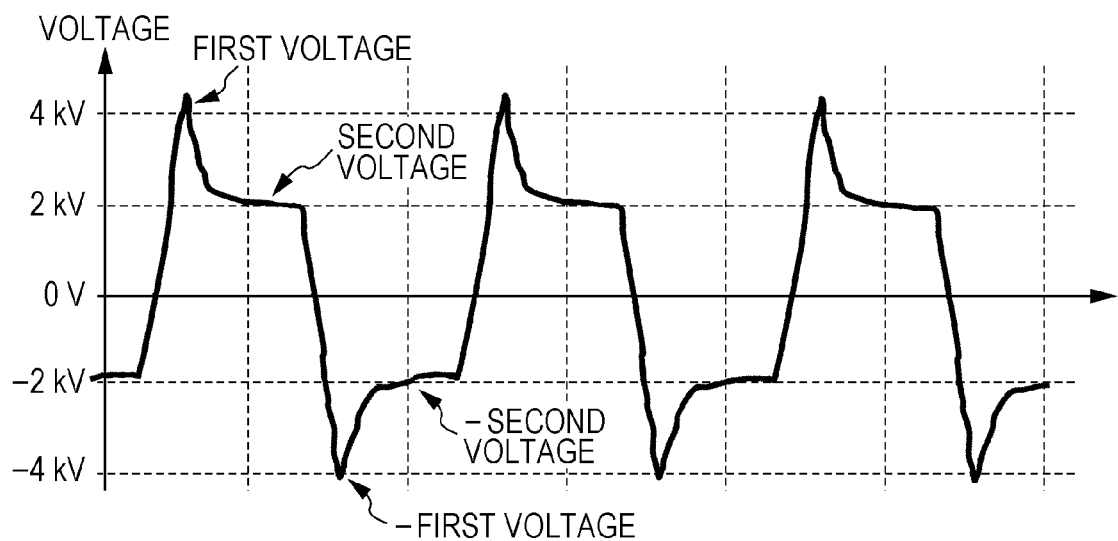
FIG. 7 is a drawing depicting an example waveform of a voltage generated between the pair of electrodes of FIG. 6.

FIG. 7 is a drawing depicting an example waveform of a voltage generated between the pair of electrodes of FIG. 6. Compared to FIG. 3, in FIG. 7, a voltage waveform in which sections including the first voltage and the second voltage (a voltage waveform in which the switch control signal corresponds to an H section in FIG. 4) are inverted appears also on the minus side. The minus-side voltage waveform also has a minus first voltage and a minus second voltage.

In the first embodiment, the discharge between the pair of electrodes occurred only in high-level sections of the switch control signal cont. In contrast, in embodiment 2, the discharge between the pair of electrodes occurs in high-level sections and low-level sections of the switch control signal cont.

In this way, in embodiment 2, the number of times that discharge occurs between the pair of electrodes doubles, and the discharge polarity between the pair of electrodes inverts each time. The speed of the discharge can be increased due to the doubling of the number of times that discharge occurs. It is thought that a greater number of types of active species are generated due to the discharge polarity between the pair of electrodes inverting each time.

As described hereinabove, according to the plasma generation device 100 in the present embodiment, compared to embodiment 1, the number of times that discharge occurs can be doubled, and the discharge polarity between the pair of electrodes can be inverted each time.

Embodiment 3

In embodiment 2, an example configuration was described in which pulses are applied to both sides of the middle tap b (namely between the middle tap b and the other end c, and between the middle tap b and the one end a) of the primary winding of the step-up transformer 20, and the discharge polarity is inverted each time. In embodiment 3, an example configuration is described in which pulses are applied to both sides of the middle tap b of the primary winding of the step-up transformer 20, and the discharge polarity is not inverted.

Figure 8:
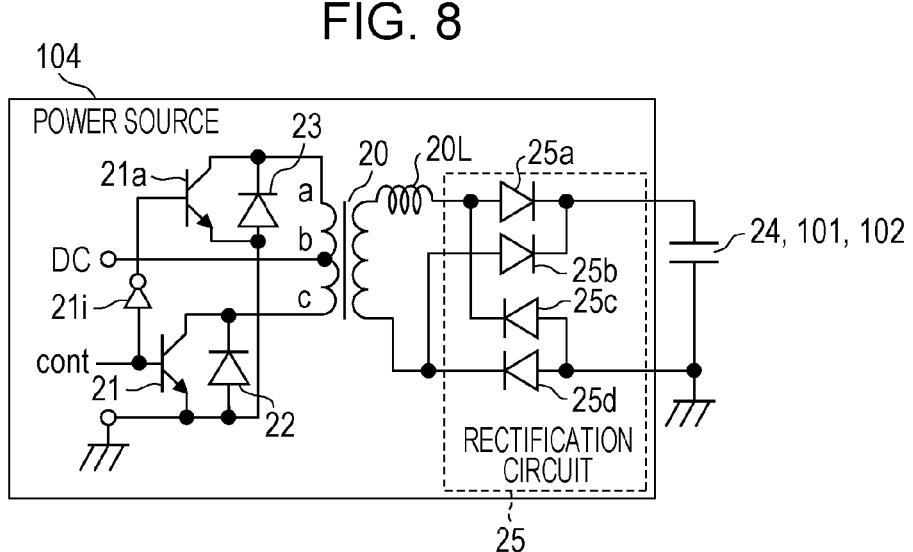
FIG. 8 is a circuit diagram depicting an example configuration of a power source and a capacitive load in embodiment 3.

FIG. 8 is a circuit diagram depicting an example configuration of the power source 104 and a capacitive load in embodiment 3. The power source 104 of FIG. 8 is different compared to FIG. 6 in that a rectification circuit 25 has been added. The remaining configuration of the power source 104 according to the present embodiment is the same as the configuration of the power source 104 according to embodiment 2. Hereinafter, the description will focus on the differences.

The rectification circuit 25 includes rectification diodes 25*a*, 25*b*, 25*c*, and 25*d*, and rectifies a voltage applied between the pair of electrodes. The rectification diodes 25*a*, 25*b*, 25*c*, and 25*d* are bridge-connected to the secondary winding of the step-up transformer 20, rectify an alternating-current voltage that is output from the secondary winding, and apply the rectified voltage between the pair of electrodes.

Figure 9:
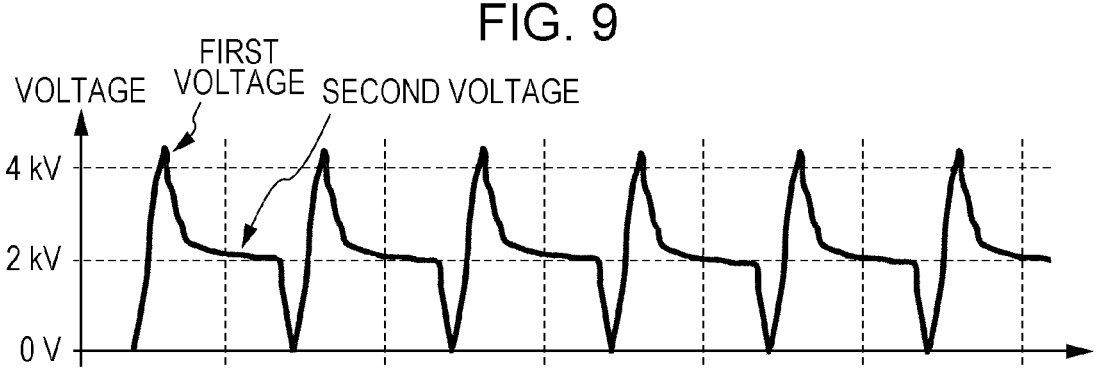
FIG. 9 is a drawing depicting an example waveform of a voltage generated between the pair of electrodes of FIG. 8.

FIG. 9 is a drawing depicting an example waveform of a voltage generated between the pair of electrodes of FIG. 8. The waveform of FIG. 9 is a waveform in which the minus side of the waveform depicted in FIG. 7 is inverted to the plus side. Consequently, the discharge polarity between the pair of electrodes is ordinarily the same and does not invert.

In this way, in the plasma generation device 100 of embodiment 3, compared to embodiment 1, the number of times that discharge occurs is doubled, and the discharge polarity is not inverted. Since the discharge polarity is not inverted, it is possible to narrow down the types of active species generated by the plasma.

Furthermore, due to the power source 104 including the rectification circuit 25, it becomes possible to switch between causing discharge with a forward voltage or a reverse voltage by altering the installation path (for example, changing between a connection with the step-up transformer and the pair of electrodes), and it is possible to realize a suppression of power consumption.

Furthermore, it is possible to limit the types of active species generated, due to the types of active species produced by plasma being different between the case where plasma is generated with both a forward voltage and a reverse voltage, and the case where plasma is generated with only one of a forward voltage or a reverse voltage.

Hereinabove, the plasma generation device 100 according to the present disclosure has been described on the basis of embodiments; however, the present disclosure is not restricted to the embodiments. Modes in which various modifications conceived by a person skilled in the art have been implemented in the present embodiments, and separate modes constructed by arbitrarily combining some the constituent elements in the embodiments or modified examples are also included within the scope of the present disclosure provided they do not depart from the purpose of the present disclosure. According to the plasma generation device 100 of the present disclosure, it is possible to realize at least one selected from the group consisting of a size reduction, cost reduction, and suppression of power consumption since it is not necessary to increase the step-up ratio itself of a step-up transformer.

The present disclosure can be used in a plasma generation device that generates a plasma liquid from water.

What is claimed is:

1. A plasma generation device comprising:
a pair of electrodes that cause plasma to be generated in atmospheric pressure by a voltage being applied between the pair of electrodes; and
a power source that includes a step-up transformer that has a coupling coefficient of 0.9 or greater and 0.9999 or less and generates the voltage,
wherein the voltage has a periodic voltage waveform having, in each period, a first voltage that generates discharge between the pair of electrodes, and a second voltage that causes the generated discharge to be maintained, and
the first voltage has an absolute value that is higher than an absolute value of the second voltage,
wherein the periodic voltage waveform has a first period and a second period that are two consecutive periods, and
the first voltage in the first period has a same polarity as the first voltage in the second period.

2. The plasma generation device according to claim 1, wherein the power source further includes a rectification circuit that rectifies the voltage applied between the pair of electrodes.

3. The plasma generation device according to claim 1, wherein the pair of electrodes are provided in a liquid, and cause the plasma to be generated in a gas-phase space in the liquid.

4. The plasma generation device according to claim 1, wherein the coupling coefficient of the step-up transformer is 0.9 or greater and 0.99 or less.

5. The plasma generation device according to claim 1, wherein the pair of electrodes cause the plasma to be generated in atmospheric pressure of 963 hPa or greater and 1063 hPa or less.

6. A plasma generation device comprising:
a pair of electrodes that cause plasma to be generated in atmospheric pressure by a voltage being applied between the pair of electrodes; and
a power source that includes a step-up transformer that generates the voltage that is applied between the pair of electrodes, and an inductor that is provided between a secondary side of the step-up transformer and the pair of electrodes, and has an inductance value of 0.01% or greater and 10% or less with respect to an inductance value of the secondary side of the step-up transformer,
wherein the voltage has a periodic voltage waveform having, in each period, a first voltage that generates discharge between the pair of electrodes, and a second voltage that causes the generated discharge to be maintained, and
the first voltage has an absolute value that is higher than an absolute value of the second voltage.

7. The plasma generation device according to claim 6, wherein the power source further includes a rectification circuit that rectifies the voltage applied between the pair of electrodes.

8. The plasma generation device according to claim 6, wherein the pair of electrodes are provided in a liquid, and cause the plasma to be generated in a gas-phase space in the liquid.

9. The plasma generation device according to claim 6, wherein the pair of electrodes cause the plasma to be generated in atmospheric pressure of 963 hPa or greater and 1063 hPa or less.

10. The plasma generation device according to claim 1, wherein the absolute value of the first voltage that generates discharge is a highest absolute value in the periodic voltage waveform in each period.

11. The plasma generation device according to claim 6, wherein the absolute value of the first voltage that generates discharge is a highest absolute value in the periodic voltage waveform in each period.

12. The plasma generation device according to claim 6, wherein the periodic voltage waveform has a first period and a second period that are two consecutive periods, and
the first voltage in the first period has a same polarity as the first voltage in the second period.

* * * * *